(12) United States Patent
Chen et al.

(10) Patent No.: US 11,207,364 B2
(45) Date of Patent: Dec. 28, 2021

(54) METHOD FOR TREATING BENIGN PROSTATIC HYPERPLASIA (BPH)

(71) Applicant: KANG PIN TECHNOLOGY CO., LTD., Pingtung County (TW)

(72) Inventors: Fu-An Chen, Pingtung County (TW); Ya-Lan Yang, Pingtung County (TW); Chun-Che Sung, Kaohsiung (TW); Yu-Syuan Huang, Pingtung County (TW)

(73) Assignee: KANG PIN TECHNOLOGY CO., LTD., Pingtung County (TW)

( * ) Notice: Subject to any disclaimer, the term of this patent is extended or adjusted under 35 U.S.C. 154(b) by 0 days.

(21) Appl. No.: 16/897,423

(22) Filed: Jun. 10, 2020

(65) Prior Publication Data
US 2020/0390839 A1 Dec. 17, 2020

(30) Foreign Application Priority Data
Jun. 12, 2019 (TW) ................................ 108120310

(51) Int. Cl.
*A61K 36/28* (2006.01)
*A61P 13/08* (2006.01)
*A61K 9/00* (2006.01)

(52) U.S. Cl.
CPC ............ *A61K 36/28* (2013.01); *A61K 9/0053* (2013.01); *A61P 13/08* (2018.01); *A61K 2236/333* (2013.01)

(58) Field of Classification Search
None
See application file for complete search history.

(56) References Cited

U.S. PATENT DOCUMENTS

| 6,428,822 B1 * | 8/2002 | Shi ........................ A61K 36/23 424/725 |
| 6,790,464 B2 | 9/2004 | Kuok et al. |
| 10,898,532 B2 * | 1/2021 | Chen ...................... A61K 36/28 |
| 2004/0142001 A1 * | 7/2004 | Kuok .................. A61K 36/328 424/195.18 |

FOREIGN PATENT DOCUMENTS

| CN | 1753682 A | 3/2006 |
| CN | 104491661 A | 4/2015 |
| JP | 05070360 | * 3/1993 |

OTHER PUBLICATIONS

Mikirova N. et al. Effect of Infla-Kine Supplementation on the Gene Expression of Inflammatory Markers in Peripheral Mononuclear Cells and on C-Reactive Protein in Blood. J of Translational Medicine 15(1)Oct. 1-8, 2017. (Year: 2017).*
Ferracane R. et al. Metabolic Profile of the Bioactive Compounds of Burdock (*Arctium lappa*) Seeds. J of Pharmaceutical and Biomedical Analysis 51:399-404, 2010. (Year: 2010).*
Shchokina Catherine, Ulanova Vera, "Investigation of antioxidant and anti-inflammatory properties of burdock thick extracts on the model of benign prostatic hyperplasia (BPHP) in rats", Received: Apr. 5, 2016, Accepted: Jun. 1, 2016, vol. 5, Journal of Molecular Pathophysiology.
Ting-Guo Kang and De-Qiang Dou, "Pharmacological Study of Burdock Seed", Research on Chinese Burdock, Sep. 2013, pp. 141-146, Liaoning Science and Technology Publishing House, China.

* cited by examiner

*Primary Examiner* — Ralph J Gitomer
(74) *Attorney, Agent, or Firm* — WPAT, PC

(57) ABSTRACT

The invention discloses a method for treating benign prostatic hyperplasia (BPH) using a burdock extract. The burdock extract is administered to a subject in need thereof to decrease prostate size of the subject. The burdock extract is obtained by extracting a sample of dried burdock seed using an extractant being water or an aqueous ethanol solution.

3 Claims, 1 Drawing Sheet

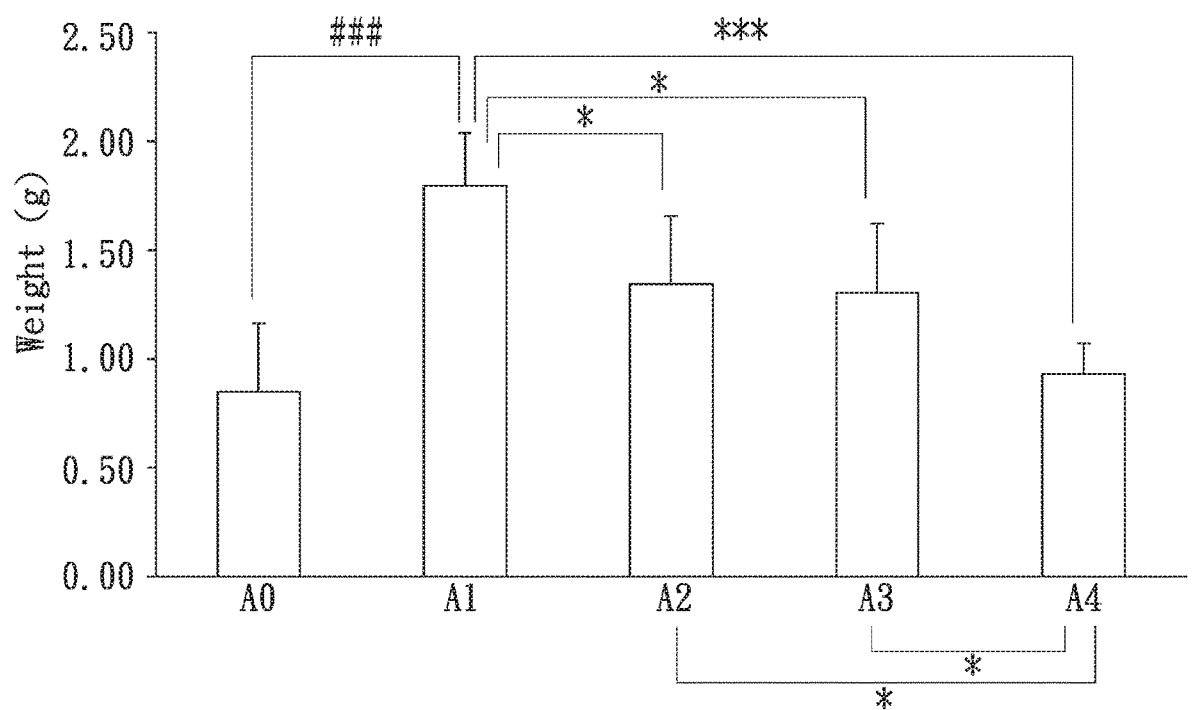

METHOD FOR TREATING BENIGN PROSTATIC HYPERPLASIA (BPH)

CROSS REFERENCE TO RELATED APPLICATIONS

The application claims the benefit of Taiwan application serial No. 108120310, filed Jun. 12, 2019, the entire contents of which are incorporated herein by reference.

BACKGROUND OF THE INVENTION

1. Field of the Invention

The present invention generally relates to a method for treating benign prostatic hyperplasia (BPH) and, more particularly, to a method for treating BPH using a burdock extract.

2. Description of the Related Art

Benign prostatic hyperplasia (BPH), also called prostate enlargement, is a common disease of middle-aged and elderly men. Symptoms may include frequent urination, trouble starting to urinate, weak stream, inability to urinate or loss of bladder control. Complications can include urinary tract infections, bladder stones and chronic kidney problems.

Treatment options include lifestyle changes, medications or surgery. In those with mild symptoms, weight loss, exercise, and decreasing caffeine intake is recommended. In those with more significant symptoms, medications may include α blockers (such as alfuzosin and doxazosin) for relaxing smooth muscle in the prostate and the bladder neck, thus decreasing the blockage of urine flow. Alternatively, 5α reductase inhibitor (such as finasteride and dutasteride) can be used to inhibit activity of dihydrotestosterone (DHT), decreasing prostate size. However, said medicaments may result in side effects such as decreased libido and ejaculatory or erectile dysfunction.

Moreover, botanical extracts from *Serenoa repens* and *Prunus africana* are considered to be effective for prostate health. Although the botanical extracts are not susceptible to side effects, raw materials produced only in Africa, the Atlantic Ocean and the Caribbean coast are difficult to access, which makes the price rise. In light of this, there is still a need to provide a method for treating BPH.

SUMMARY OF THE INVENTION

It is therefore an objective of the present invention to provide a method for treating benign prostatic hyperplasia (BPH).

It is another objective of this invention to provide a method for treating BPH using an extract derived from raw materials being easily accessed.

One embodiment of the present invention discloses a method for treating benign prostatic hyperplasia (BPH), by administering a burdock extract to a subject in need thereof to decrease prostate size of the subject. The burdock extract is obtained by extracting a sample of dried burdock seed using an extractant being water or an aqueous ethanol solution.

Accordingly, the active ingredients of the burdock extract can effectively decrease prostate size of the BPH subject. Therefore, the burdock extract can be used to be applied for manufacturing a medicament for BPH. Moreover, the burdock extract is extracted from the sample of dried burdock seed which is easily accessed in Taiwan. Thus, consumers can purchase the burdock extract with good curative effect at affordable prices. In addition, by the use of the sample of dried burdock seed, the burdock extract has a preferable effect on decreasing prostate size of the BPH subject.

In a preferred form shown, the burdock extract is obtained by extracting the sample of dried burdock seed using the aqueous ethanol solution with a concentration of ethanol being 80-98%. As such, the burdock extract has a preferable effect on decreasing prostate size of the BPH subject.

In a preferred form shown, the burdock extract is orally administered to the subject, and is preferably administered to the subject in the dosage of 900 mg/kg/day for 28-60 days. As such, the burdock extract has a preferable effect on decreasing prostate size of the BPH subject.

BRIEF DESCRIPTION OF THE DRAWINGS

The present invention will become more fully understood from the detailed description given hereinafter and the accompanying drawings which are given by way of illustration only, and thus are not limitative of the present invention, and wherein:

Sole FIGURE depicts a bar chart illustrating prostate weight of the rats of groups A0-A4.

DETAILED DESCRIPTION OF THE INVENTION

Burdock (*Arctium lappa*) is a biennial plant which belongs to the family of Asteraceae and the genus of *Arctium*, and is planted in Gueilai, Pingtung during the period of Japanese Taiwan. Root of burdock contains dietary fibers and polyphenols, and is considered to be effective on lose weight and health. Leaf of burdock is rich in carotene and vitamin C, and can help enhance immunity. Dried seed of burdock including active ingredients such as arctiin and arcitigenin can be used to be diuretic and antipyretic.

A burdock extract according to an embodiment of the present invention can refer to a product obtained by extracting a sample of burdock by an extractant. The extractant can be water or an aqueous ethanol ($EtOH_{(aq)}$), preferably be the aqueous ethanol solution with a concentration of ethanol being 80-98%. As an example, a worker can mix the extractant (500-2,000 mL) with the sample of burdock (100 grams). Extraction is carried out under boiling conditions for 0.5-6 hours to obtain a supernatant. The supernatant is then filtered, concentrated at a reduced pressure, and frozen dried to form the burdock extract.

Specifically, the sample of burdock can be a sample of burdock root, a sample of burdock leaf or a sample of dried burdock seed. The sample of burdock can be preferably dried in advance to obtain a dried sample of burdock with a water content less than 15%. Besides, the sample of burdock can also be cut into slices with a thickness of 0.1-0.5 cm, or be milled to particles with a size smaller than 2 mm in advance as well. With such performance, the contacting surface area of the sample of burdock with the extractant is increased, and therefore, the efficiency of the extraction is also increased.

In the first embodiment, 100 grams of the sample of burdock root is mixed with 1,000 mL of the 95% aqueous ethanol solution (the aqueous ethanol solution with the concentration of ethanol being 95%). The extraction carried out under boiling conditions for 3 hours. After filtration, concentration at a reduced pressure, and frozen drying, about 4-6 grams of the burdock extract is obtained. In the second, third embodiment, the sample of burdock root used in the first embodiment is replaced with the sample of burdock leaf and the sample of dried burdock seed, respectively. The obtained burdock extracts are about 7-13 grams and about 10-12 grams, respectively. For clarification, the burdock extracts in the first, second and third embodiments are named a burdock root extract, burdock leaf extract and a dried burdock seed extract, respectively.

The burdock extract can effectively decrease prostate size of a BPH subject. Therefore, the burdock extract can be used to be applied for manufacturing a medicament for BPH. The burdock extract can be used in combination with pharmaceutical acceptable vehicles, excipients, salts or other nutrients, forming a pharmaceutical composition. In addition, burdock extract can be further manufactured into any oral type that is easy to take, such as pastil, capsule, powder, pill or solution.

Moreover, the burdock extract can be administered to the subject in a dosage of 900 mg/kg/day for 28-60 days, as an example. Thus, the active ingredients of the burdock extract can effectively decrease prostate size of the BPH subject.

Sprague-Dawley rats (SD rats, 6 week-old) purchased from BioLASCO Taiwan Co., Ltd are used. The rats are housed in an animal room with constant temperature of 22±2° C., where is kept on a 12-hours light and 12-hours dark cycle. The rats are housed and kept on free diet and water.

Referring to TABLE 1, for inducing rats with benign prostatic hyperplasia (BPH rats), testosterone is subcutaneous injected to castrated rats in the dosage of 10 mg/kg/day for 28 days.

TABLE 1

| Group | Rat | burdock extract |
|---|---|---|
| A0 | normal rat | none |
| A1 | BPH rat | none |
| A2 | BPH rat | burdock root extract |
| A3 | BPH rat | burdock leaf extract |
| A4 | BPH rat | dried burdock seed extract |

At the same time, the burdock root extract, the burdock leaf extract and the dried burdock seed extract are orally administered to the BPH rats of groups A2-A4, respectively in the dosage of 900 mg/kg/day for 28 days. The normal rats of group A0, as well as the BPH rats of groups A1, are orally administered by 0.5% carboxymethyl cellulose (CMC) solution (dissolved in water).

Referring to the Sole FIGURE, 28 days later, the prostates of the rats of groups A0-A4 are weighted. The prostates of the normal rats of group A0 have an average weight of 0.84±0.34 grams, the prostates of the BPH rats of group A1 have an average weight of 1.80±0.24 grams, showing significant difference from the prostates of the normal rats of group A0 ("###", $P<0.001$). Moreover, compared to the prostates of the BPH rats of group A1 orally administered by the CMC solution, the BPH rats of group A2-A4 orally administered by the burdock root extract, the burdock leaf extract and the dried burdock seed extract have the lighter prostates with the average weight being 1.34±0.31 grams, 1.30±0.32 grams and 0.93±0.14 grams, respectively ("*", $P<0.05$; "***", $P<0.001$), indicating the burdock extract can be used to decrease prostate size of the BPH subject.

It is worthy to note that compared to the prostates of the BPH rats of group A2 orally administered by the burdock root extract and the prostates of the BPH rats of group A3 orally administered by the burdock leaf extract, the BPH rats of group A4 orally administered by the dried burdock seed extract have a lighter prostate ("*", $P<0.05$). Moreover, the BPH rats of group A4 orally administered by the dried burdock seed extract have the prostates with similar weight to the prostates of the normal rats of group A0 ($P>0.05$), indicating that the dried burdock seed extract has a preferable effect compared to the burdock root extract and burdock leaf extract.

Accordingly, the active ingredients of the burdock extract can effectively decrease prostate size of the BPH subject. Therefore, the burdock extract can be used to be applied for manufacturing a medicament for BPH.

Moreover, the burdock extract is extracted from the sample of dried burdock seed which is easily accessed in Taiwan. Thus, consumers can purchase the burdock extract with good curative effect at affordable prices.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for treating benign prostatic hyperplasia (BPH), comprising:
   administering an effective amount of a burdock extract to a subject in need thereof to decrease prostate size of the subject, wherein the burdock extract is obtained by extracting a sample of dried burdock seed using an extractant being an aqueous ethanol solution with a concentration of ethanol being 95% under boiling condition.

2. The method for treating BPH as claimed in claim 1, wherein the burdock extract is orally administered to the subject.

3. The method for treating BPH as claimed in claim 2, wherein the burdock extract is administered to the subject in the effective amount of 900 mg/kg/day for 28-60 days.

* * * * *